United States Patent [19]

Mikkelsen

[11] Patent Number: Plant 5,875

[45] Date of Patent: Feb. 10, 1987

[54] KALANCHOE PLANT NAMED FLAMBOYANT

[75] Inventor: James C. Mikkelsen, Ashtabula, Ohio

[73] Assignee: Mikkelsens, Inc., Ashtabula, Ohio

[21] Appl. No.: 712,112

[22] Filed: Mar. 15, 1985

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Schwartz, Jeffery, Schwaab, Mack, Blumenthal & Evans

[57] ABSTRACT

A new and distinct cultivar of Kalanchoe plant named Flamboyant, characterized by its distinct light orange flower color, dense symmetrical foliage and branching, early and floriferous flowering habit, and its excellent keeping qualities.

1 Drawing Figure

The present invention relates to a new and distinct cultivar of Kalanchoe plant, botanically known as *Kalanchoe blossfeldiana,* and known by the cultivar name Flamboyant. Flamboyant was developed by me through controlled breeding by crossing Mikkelsen seedling No. 79-2273-1 (seed parent) and Mercur (pollen parent). Mercur is disclosed in U.S. Plant Pat. No. 5,347.

Asexual reproduction by stem cuttings has shown that the unique features of this new Kalanchoe are stabilized and are reproduced true to type in successive propagations.

The following characteristics distinguish the new Kalanchoe from both its parent cultivars and other cultivated Kalanchoes of this type known and used in the floriculture industry:

1. Flamboyant is lighter in color than the female parent Mercur or Regulus (disclosed in U.S. Plant Pat. No. 4,817, or Rhumba (disclosed in U.S. Plant Pat. No. 4,307). The flower size of Flamboyant is larger than Mercur and Rhumba and similar to Regulus.

2. Branching is superior to Rhumba and Mercur and equal to Regulus.

3. Plant growth is slow compared to Rhumba, but similar to Regulus and Mercur.

4. Flowering time is 8 weeks in summer to 12 weeks in winter after the start of short days, as compared to Mercur which is 11 weeks in summer and 13 weeks in winter, and Regulus which is 13 weeks in summer and 14 weeks in winter, all as tested in Ashtabula, Ohio.

5. Foliage crenation is not as deep as Rhumba, which is almost dentate, and Regulus, and is similar to Mercur.

6. The plant has shorter internodes than Rhumba and is denser with more leaves than Regulus and Mercur. Plants are more symmetrical than Regulus and Mercur.

7. After flower initiation plants must be treated with B-9 in all seasons to reduce peduncle elongation.

8. Pedicels are longer than Mercur, but similar to Regulus in length on the terminal flower cluster.

9. Leaves are broader and lighter green in color than either Mercur or Regulus.

10. Moderate growth rate, symmetrical branching and dense foliage make Flamboyant highly suited for 10 cm pot production.

11. The number of flowers are greater than Rhumba and Mercur but similar to Regulus, both on the terminal cluster and lateral clusters. Flamboyant has large symmetrical flower clusters.

The accompanying colored photograph, taken in February of 1985, illustrates in perspective view the overall appearance of Flamboyant, showing the colors as true as it is reasonably possible to obtain in a colored reproduction of this type.

The following is a detailed description of my new Kalanchoe cultivar grown in 10 cm plastic pots produced under commercial practices in the greenhouses of Mikkelsens Inc., Ashtabula, Ohio. Color references are made to The Royal Horticultural Society Colour Chart except where general terms of ordinary dictionary significance are used.

Parentage: A controlled cross between Mikelsen seedling No. 79-2273-1 and Mercur.

Propagation:

(A) *Type cutting.*—Short stem cutting up to 2 cm long; propagates easily and in great quantity from stock plants.

(B) *Time to root.*—10 days at 21° C. summer, 14 days at 21° C. winter.

(C) *Rooting habit.*—Many fine fibrous roots.

Plant description:

(A) *Form.*—Compact, upright, well branched; best suited for growing and scheduling practices for 10 cm pots.

(B) *Habit of growth.*—Moderate rate of growth with branching from nearly every node.

(C) *Foliage.*—Leaves simple, opposite. (1) Size: Average full grown leaf of plant in flowering in a 10 cm pot is 100 mm long and 70 mm wide. (2) Shape: Ovate, apex obtuse, base attenuate. (3) Texture: Glabrous, coriaceous, succulent. (4) Margin: Crenate. (5) Color: young foliage, top side green 137A, under side green 137C. Mature foliage, top side yellow-green 147A, under side green 137A.

Flowering description:

(A) *Flowering habits.*—Cyme inflorescence on terminal branches and laterals. Each shoot is formed by dichotomous branching starting with the opening of the terminal flowers of the main axis, followed by terminal flowers of the side branching, continuing with subsequent development of branching in the inflorescence. Major inflorescence is 80 mm in diameter and lateral inflorescences are 60 to 70 mm in diameter.

(B) *Natural flowering season.*—Early January. Flowering time under controlled daylength at 20° C. in summer is 8 weeks; in winter is 12 weeks. Flowering time depends on temperature, light intensity, and other growing conditions.

(C) *Flower buds.*—Oblong, up to 6 mm long, developing to tubular as flower petals mature, sheathed with four light green sepals; corolla at maturity is 12 mm long.

(D) *Flowers borne.*—Terminal and lateral branches are compound dichasial; peduncle 4 mm in diameter, with peduncle length depending on growing conditions and B-9 application; pedicels up to 13 mm long.

(E) *Quantity of flowers.*—Highly floriferous; main axis has over 100 flowers, side branches over 50 flowers with 8 to 10 side brances in a 10 cm pot; excellent keeping quality.

(F) *Petals.*—(1) Shape: Nearly rounded, top cuspidate. (2) Color: Top side when opening orange 25A with streaks of 28B, changing to range-red 24A-B; under side orange 24C with streaks of orange-red 30C. (3) Number of petals: Four (4).

(G) *Reproductive organs.*—(1) Stamens: Eight (8) in number. (a) Anther shape: Flat elliptical, color yellow. (b) Filament color: Light green. (c) Pollen color: Yellow. (2) Pistels: (a) Stigma: Flat, immature color greenish white, mature color white. (b) Styles: Light green. (c) Ovaries: 4 celled, 7 mm in size, color light green.

Disease resistance: Highly resistant to Mildew. No other disease problems seen to date.

I claim:

1. A new and distinct cultivar of Kalanchoe plant named Flamboyant, as illustrated and described, and particularly characterized by its distinct light orange flower color, dense symmetrical foliage and branching, early and floriferous flowering habit, and its excellent keeping qualities.

* * * * *

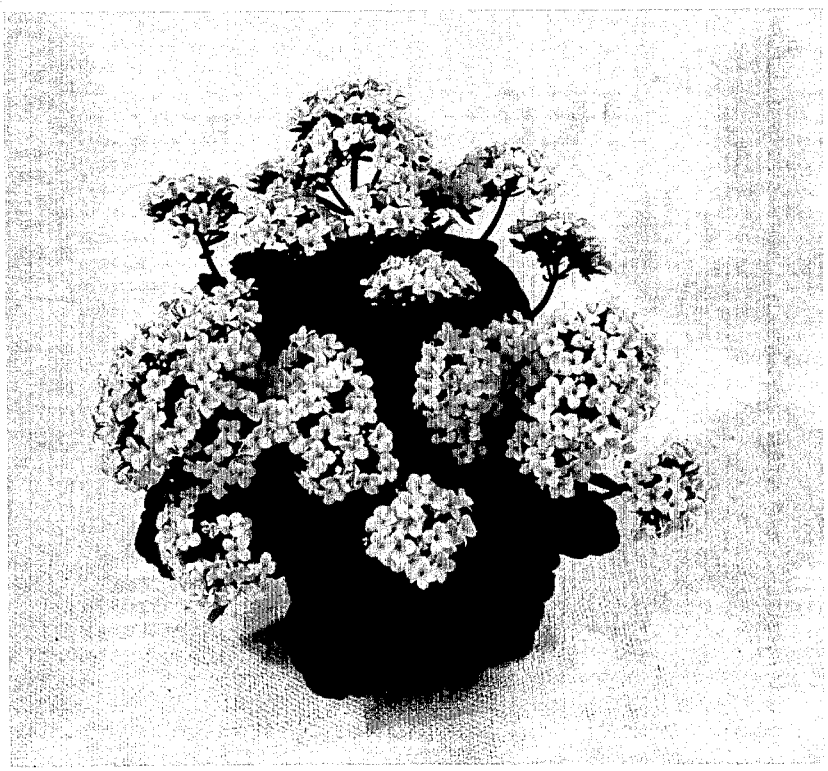

FLAMBOYANT